(12) United States Patent
Raupach et al.

(10) Patent No.: US 10,517,547 B2
(45) Date of Patent: Dec. 31, 2019

(54) DIAPHRAGM APPARATUS FOR THE COLLIMATION OF AN X-RAY BUNDLE OF AN X-RAY DEVICE

(71) Applicant: Siemens Healthcare GmbH, Erlangen (DE)

(72) Inventors: Rainer Raupach, Heroldsbach (DE); Michael Grasruck, Nuermberg (DE); Nicole Haag, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 221 days.

(21) Appl. No.: 15/451,530

(22) Filed: Mar. 7, 2017

(65) Prior Publication Data

US 2017/0273645 A1   Sep. 28, 2017

(30) Foreign Application Priority Data

Mar. 23, 2016  (DE) .................. 10 2016 204 870

(51) Int. Cl.
| | |
|---|---|
| *A61B 6/06* | (2006.01) |
| *G21K 1/02* | (2006.01) |
| *A61B 6/03* | (2006.01) |
| *A61B 6/00* | (2006.01) |

(52) U.S. Cl.
CPC ............. *A61B 6/06* (2013.01); *G21K 1/025* (2013.01); *A61B 6/032* (2013.01); *A61B 6/4441* (2013.01)

(58) Field of Classification Search
CPC . A61B 6/06; G21K 1/02; G21K 1/025; G21K 1/04
See application file for complete search history.

(56) References Cited

U.S. PATENT DOCUMENTS

| | | | | |
|---|---|---|---|---|
| 4,277,685 A | * | 7/1981 | Covic | ................... G03B 42/02 378/150 |
| 4,404,591 A | | 9/1983 | Bonar | |
| 4,581,753 A | | 4/1986 | Grady | |
| 4,715,056 A | | 12/1987 | Vlasbloem | |
| 4,788,699 A | * | 11/1988 | Dobert | ..................... A61B 6/06 378/147 |
| 5,134,642 A | | 7/1992 | Van Elburg | |

(Continued)

FOREIGN PATENT DOCUMENTS

DE            68919220 T2        5/1995

OTHER PUBLICATIONS

German Office Action dated Jan. 11, 2017.

*Primary Examiner* — Thomas R Artman
(74) *Attorney, Agent, or Firm* — Harness, Dickey & Pierce, P.L.C.

(57) ABSTRACT

A diaphragm apparatus for the collimation of an X-ray bundle of an X-ray device is provided for scanning an examination object. An X-ray device including the diaphragm apparatus is also provided. In an embodiment, the diaphragm apparatus includes two diaphragms in the form of slotted diaphragms arranged in series in the direction of the X-rays and mounted to be positionable with respect to one another. Each of the diaphragms includes a fixed diaphragm aperture corresponding to maximum collimation of the X-ray bundle and a region that is impermeable to X-rays, which in each case includes an extension corresponding to the diaphragm aperture corresponding to the maximum collimation.

26 Claims, 2 Drawing Sheets

(56) References Cited

U.S. PATENT DOCUMENTS

| | | | | |
|---|---|---|---|---|
| 5,644,614 A * | 7/1997 | Toth | ............... | A61B 6/032 378/145 |
| 6,396,902 B2 * | 5/2002 | Tybinkowski | ......... | G21K 1/025 378/148 |
| 7,068,751 B2 * | 6/2006 | Toth | ............... | A61B 6/032 378/20 |
| 7,403,597 B2 * | 7/2008 | Raupach | ............ | A61B 6/032 378/145 |
| 9,263,160 B2 * | 2/2016 | Kang | ............... | G21K 1/025 |
| 10,123,756 B2 * | 11/2018 | Karch | ............... | G21K 1/10 |
| 2005/0089138 A1 * | 4/2005 | Toth | ............... | A61B 6/032 378/20 |
| 2006/0262897 A1 * | 11/2006 | Raupach | ............ | A61B 6/032 378/16 |
| 2014/0119508 A1 * | 5/2014 | Kang | ............... | G21K 1/025 378/62 |

\* cited by examiner

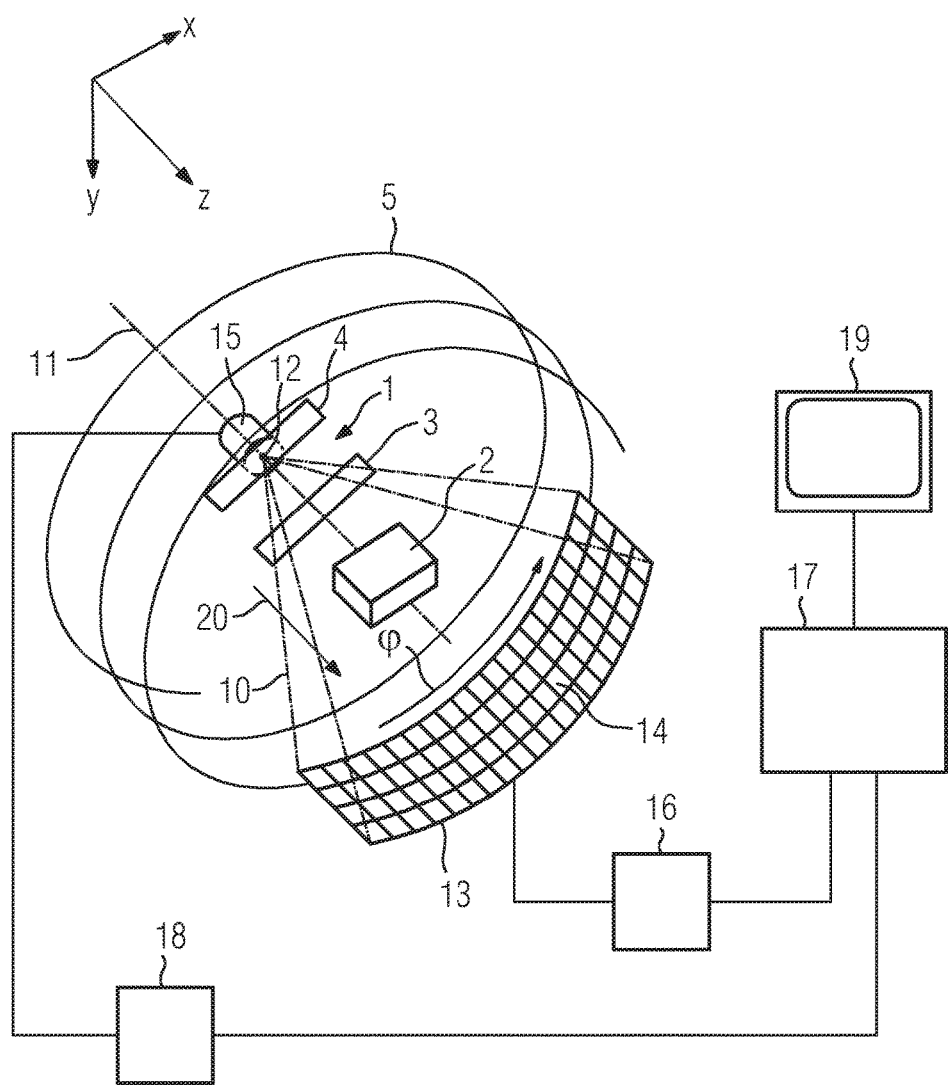

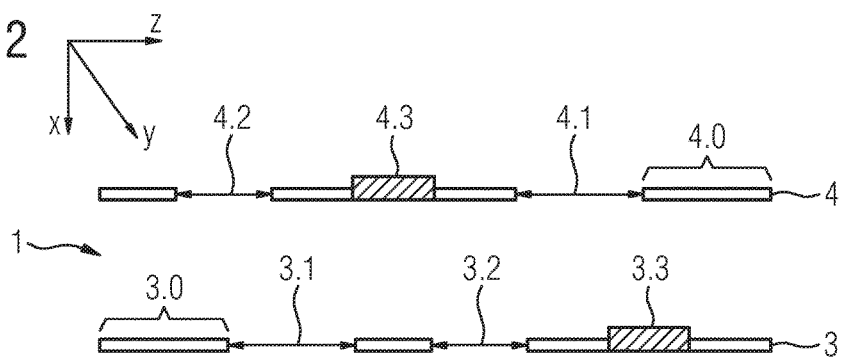
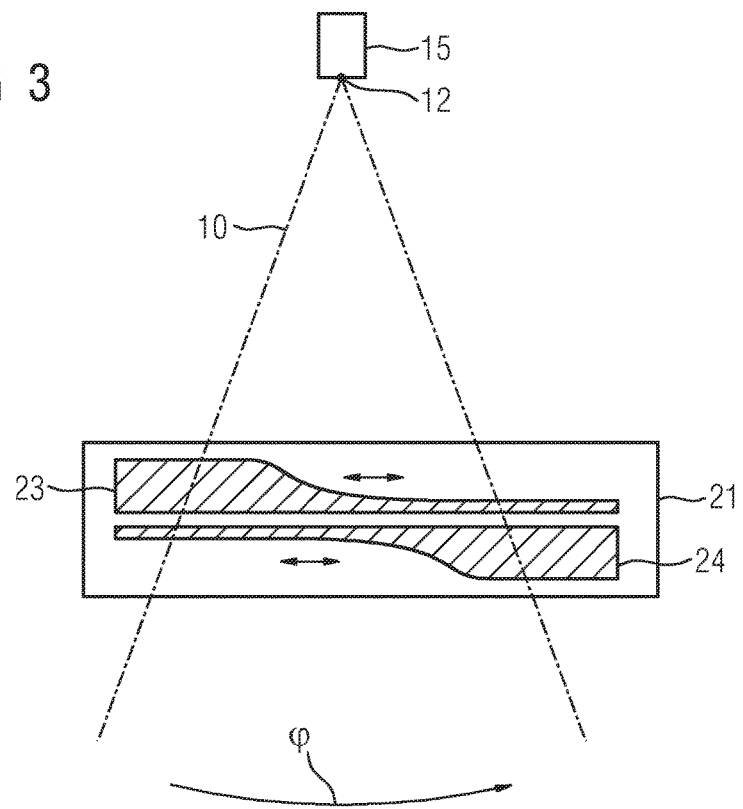

DIAPHRAGM APPARATUS FOR THE COLLIMATION OF AN X-RAY BUNDLE OF AN X-RAY DEVICE

PRIORITY STATEMENT

The present application hereby claims priority under 35 U.S.C. § 119 to German patent application number DE 102016204870.8 filed Mar. 23, 2016, the entire contents of which are hereby incorporated herein by reference.

FIELD

At least one embodiment of the invention generally relates to a diaphragm apparatus for the collimation of an X-ray bundle of an X-ray device provided for scanning an examination object and/or an X-ray device comprising a diaphragm apparatus of this kind.

BACKGROUND

The collimation or overlaying of X-rays should generally be understood to be the adaptation of the X-ray bundle emitted by X-ray source of the X-ray system to the scan field of view of the X-ray detector used. In this context, the term is not restricted to one of the system axes of the X-ray system. Hence, collimation can be implemented in the feed direction of the X-ray device, if provided, or along a system direction perpendicular thereto, for example in the fan direction of a computed tomography system or in any direction. In principle, collimation is used to reduce the X-ray dose for the examination object and is hence an essential operating instruction for all medical imaging procedures in the sense of the ALARA principle. In addition, suitable collimation generally enables X-ray detector overbeaming to be achieved and generally stray radiation to be suppressed.

Nowadays, the overlaying of X-rays in X-ray systems for medical imaging, such as, for example, computed tomography systems or C-arm X-ray devices is in principle performed in two different ways. On the one hand, fixed diaphragms with unchangeable diaphragm apertures are used, which typically do not allow the passage of at least an outer sub-region of an X-ray bundle depending on size and position relative to the X-ray, by way of absorption in the diaphragm material. Only the part of the X-rays allowed to pass reaches the examination object in the further beam path and is used for imaging. Fixed diaphragms save costs and space since a plurality of diaphragm apertures with different sizes can be arranged on a diaphragm in the positioning direction and, depending upon the application, can be moved into or out of the X-ray via a single drive. However, they have the drawback with respect to the size of diaphragm apertures that only a few inflexible variants are available for selection and these are not optimally suitable for each examination using an X-ray device.

On the other hand, use is made of diaphragm blades that can be moved or positioned separately with respect to one another and which enable the individual, and in particular dynamic, adjustment of the size of a diaphragm aperture. With diaphragms of this kind, it is even possible to vary the size of the diaphragm dynamically during an X-ray examination in order advantageously to keep the dose to which a patient is exposed as low as possible. Obviously, this requires positioning mechanisms with sufficient speed and precision, which, as a rule, entails increased production costs for the X-ray system. In addition, more installation space is required.

In addition, in order to reduce the total dose applied or stray radiation and to avoid detector overbeaming, it is also desirable to adapt the intensity profile or the energy spectrum of the X-rays to the special circumstances of an X-ray examination within the X-ray bundle. To this end, it is possible to use filters in the form of intensity filters (depending on their shape, so-called wedge or bowtie filters) or spectral filters (for example an Sn filter). The filters are characterized in that, due to the generally partial absorption of the X-rays, they attenuate the intensity of the X-rays or only absorb X-rays with a specific energy or do both simultaneously. To adapt the intensity profile, the filter use has to be adapted exactly to the absorption profile of the examination object in order to the keep the dose to which the examination object is exposed as low as possible.

If required, in modern X-ray systems, these filters can also be introduced into the X-ray beam.

SUMMARY

The inventors have recognized that, at present, costs and space requirements restrict the individual adaptability of an intensity profile filter to an examination object. Therefore, although it is known to provide a plurality of different wedge filters in an X-ray system in series in the positioning direction that can be introduced in the X-rays via a drive in the X-rays, as a rule these do not take sufficient account of the individual circumstances of the examination object.

At least one embodiment of the present invention provides a diaphragm apparatus that overcomes the existing drawbacks of the prior art and can be used particularly flexibly.

Embodiments of the present invention are directed to apparatuses described herein, in particular as claimed in the independent claims. Developments and advantageous variants are in each case the subject matter of the dependent claims.

At least one embodiment according to the invention is directed to a diaphragm apparatus. Features, advantages or alternative embodiments mentioned in this can likewise be transferred to the other claimed subject matter and vice versa.

At least one embodiment of the invention relates to a diaphragm apparatus for a collimation of an X-ray bundle of an X-ray device provided for scanning an examination object. The diaphragm apparatus comprises two diaphragms in the form of slotted diaphragms arranged in series in the direction of the X-rays and mounted so as to be positionable with respect to one another. Each of the diaphragms has a fixed diaphragm aperture corresponding to maximum collimation of the X-ray bundle and a region that is impermeable to X-rays, which in each case has an extension corresponding to the diaphragm aperture corresponding to the maximum collimation.

At least one embodiment of the invention further relates to a filter apparatus for forming an intensity profile of the X-ray bundle. This filter apparatus may have a filter which, in turn, has one or more filter elements.

This filter apparatus can be combined with the above-described diaphragm apparatus. However, the filter apparatus represents an individual aspect of at least one embodiment of the invention, which is also disclosed herein independently of the diaphragm apparatus and can be used independently. To form an intensity profile of the X-ray bundle, the filter apparatus according to an embodiment of the invention comprises two filter elements mounted so as to be positionable with respect to one another and to be arrangeable in series in the X-ray direction, which are in each case shaped such that that, as soon as they are arranged completely superimposed in the X-ray direction, they form a complete filter profile.

At least one embodiment of the invention further relates to an X-ray device for scanning an examination object via an X-ray bundle comprising a diaphragm apparatus according to at least one embodiment of the invention.

In one particularly preferred variant of at least one embodiment, the X-ray device is embodied as a computed tomography device or a C-arm X-ray device.

In one particularly preferred variant of at least one embodiment, the medical imaging system is embodied as an X-ray computed tomography scanner or as a C-arm X-ray device.

BRIEF DESCRIPTION OF THE DRAWINGS

The above-described properties, features and advantages of this invention and the manner in which they are achieved become clearer and more distinctly comprehensible in connection with the following description of the example embodiments which are explained in more detail with reference to the drawings. This description does not restrict the invention to these example embodiments. The same components are given identical reference characters in different figures. The figures are, as a rule, not true to scale and show:

FIG. 1 an X-ray device in the form of a computed tomography scanner according to an example embodiment of the invention, FIG. 2 an example embodiment of the diaphragm apparatus according to the invention, FIG. 3 an example embodiment of the filter apparatus according to the invention, and

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a diaphragm apparatus for a collimation of an X-ray bundle of an X-ray device provided for scanning an examination object. The diaphragm apparatus comprises two diaphragms in the form of slotted diaphragms arranged in series in the direction of the X-rays and mounted so as to be positionable with respect to one another. Each of the diaphragms has a fixed diaphragm aperture corresponding to maximum collimation of the X-ray bundle and a region that is impermeable to X-rays, which in each case has an extension corresponding to the diaphragm aperture corresponding to the maximum collimation.

The following assumes with respect to at least one embodiment of the present invention, without limiting generality, that the examination object is a patient, in most cases usually a human. However, the patient can in principle also be an animal. Hence, in the following the two terms "examination object" and "patient" are also used synonymously. However, the examination object can also be a plant or an inanimate object, for example a historical artifact or the like.

Consequently, the two diaphragms in the diaphragm apparatus according to at least one embodiment of the invention comprise an aperture permeable to X-rays. This aperture comprises an extension in the positioning direction of the diaphragms corresponding to maximum collimation of the X-ray bundle. In other words, a diaphragm aperture corresponding to maximum collimation clips a minimal part of the X-ray bundle which is then unable to pass the diaphragm aperture. Consequently, the diaphragm aperture corresponding to maximum collimation indicates the greatest possible collimation that can be set with the diaphragm apparatus according to at least one embodiment of the invention. Further diaphragm apertures that may optionally be present on the diaphragms for the collimation of the X-ray bundle have a smaller extension at least in the positioning direction and allow a smaller part of the X-ray bundle to pass.

The diaphragm apertures corresponding to maximum collimation preferably have the same extension on both diaphragms.

Each of the diaphragms further also comprises a region that is impermeable to X-rays. This region is in each case the same size as the diaphragm aperture corresponding to a maximum collimation and characterized in that X-rays incident in this region are almost completely, i.e. substantially 100 percent, absorbed. In other words, the incident X-rays are unable to pass through this region.

If the position of the two diaphragms is set such that both apertures corresponding to a maximum collimation coincide in the direction of radiation, i.e. are superimposed, the maximal possible proportion of the X-ray bundle is able to pass through the diaphragm apparatus. If the position of the two diaphragms is adjusted such that a diaphragm aperture corresponding to the maximum collimation and a region that is impermeable to X-rays coincide in the direction of radiation, the X-ray bundle can be substantially completely masked out. In other words, in this case, no X-rays reach the examination object any longer.

A displacement or positioning of the two diaphragms relative to one another between these extreme arrangements described can now enable any degree of collimation between complete masking out of the X-ray bundle and maximum collimation to be achieved.

At least one embodiment of the present invention is consequently based on a combination of properties of a slotted diaphragm and properties of individually adjustable diaphragm blades so that two slotted diaphragms and two drives enable very flexible overlaying of X-rays which are optimally adapted to the examination object or the desired examination.

In one variant of at least one embodiment of the present invention, the region that is impermeable to X-rays of one diaphragm is arranged in respect of the positioning direction on one side of the diaphragm aperture corresponding to the maximum collimation and the region that is impermeable to X-rays of the other diaphragm is arranged in respect of the positioning direction on the other side of the diaphragm aperture corresponding to the maximum collimation.

In other words, one diaphragm comprises the region impermeable to X-rays region on one side of the diaphragm aperture, while the region that is impermeable to X-rays of the other diaphragm lies on the opposite side of the corresponding diaphragm aperture.

The diaphragm aperture corresponding to the maximum collimation and the region impermeable to X-rays of each diaphragm are preferably directly adjacent to one another on a diaphragm. Regardless of the sequence of the diaphragms in the beam path, this embodiment enables any type of collimation of an X-ray bundle, in particular also collimation which is not symmetrical about the central beam of the X-ray bundle, since in this embodiment either the left or right edge of a diaphragm aperture of diaphragm is advantageously able to interact with the respective opposite edge of diaphragm aperture of the other diaphragm.

Depending upon which part of the X-ray bundle is to be masked out, in this embodiment, the collimation can be achieved particularly easily by positioning only one of the diaphragms.

The adjustment of the collimation can take place particularly quickly by way of shorter traverse or positioning paths; the shorter positioning paths enable the installation space to be kept low.

According to an alternative embodiment of the present invention, at least one of the two diaphragms of the diaphragm apparatus comprises a further fixed diaphragm aperture corresponding to a collimation smaller than the maximum collimation.

Consequently, one of the diaphragms is embodied as a slotted diaphragm with at least two slotted diaphragm apertures, wherein the further fixed diaphragm aperture has an extension in the positioning direction that is smaller than the extension of the diaphragm aperture corresponding to the maximum collimation. In other words, as long as it is positioned in the X-ray path, the further fixed diaphragm aperture masks out a larger part of the X-ray bundle than the diaphragm aperture corresponding to maximum collimation.

This further diaphragm aperture can also interact with the region impermeable to X-rays of the other diaphragm. This also advantageously enables the achievement of short positioning paths, wherein, instead of positioning both diaphragms, one of them can also be fixed and only the respective other one moved. Short positioning paths in principle also have an advantageous effect on the positioning times so that the collimation of the X-ray bundle can also be set quickly and precisely during an X-ray examination, for example, in dependence on an angle of rotation of the X-ray system or in dependence on a scanning time with a higher speed.

Preferably in at least one embodiment, the two diaphragms comprise more than one diaphragm aperture with extensions differing from one another in the positioning direction. As a result, any number of individually adjustable collimations is conceivable and adjustable.

One preferred variant of at least one embodiment of the invention provides that the two diaphragms are mounted parallel so as to be positionable with respect to one another. This in particular enables a situation-dependent adaptation of the diaphragm apparatus to the beam geometry of the recording system of the X-ray device, which is, for example, necessary and advisable, when the focus of the X-ray source is displaced due to thermal stresses.

As mentioned in the introduction, the overlaying of the X-rays is not restricted to a specific axis of the X-ray system. However, according to a particularly preferred embodiment of the invention, the two diaphragms are mounted movably along the and/or transverse to a feed direction of the X-ray device. A feed direction indicates the direction, in which scanning of an examination object takes place if the region of the examination object to be depicted or the body part to be depicted cannot be acquired completely by way of circumnavigation via the X-ray device. In such a case, the X-ray device is, for example, a computed tomography device.

If positionability is provided along the feed direction of the X-ray device, particularly preferably a dynamic adaptation of the collimation can be performed during an examination via an X-ray device in order to protect the examination object from unnecessary X-rays during after-run times and/or run-in times. If positionability of the diaphragms is provided transverse to a feed direction, the collimation can in particular be adapted in the fan direction of the X-rays, for example to the changing width of the examination object or the region or body part to be depicted in the positioning direction during the rotation of the X-ray device about the examination object. This also avoids an unnecessary dose or stray radiation.

According to one variant of at least one embodiment of the invention, the collimation of the X-ray bundle can be adjusted by way of only one diaphragm. In this case, only one of the two diaphragms with one of its slotted apertures of the desired extension is used for the overlaying. This procedure is particularly suitable for simpler applications in which, for example, there is no need for dynamic adaptation during an acquisition of image data. Consequently, an embodiment of the invention also enables the implementation of applications of this kind. Moreover, this variant enables the use of the respective other diaphragm for further filter applications in order advantageously to influence the X-rays, as is described in more detail below.

According to an alternative and preferred variant of at least one embodiment of the invention, the collimation of the X-ray bundle can be adjusted via both diaphragms. As explained in the introduction, this takes place by way of a flexible and dynamic interaction of the diaphragm apertures or, for regions impermeable to X-rays, on the diaphragms. Dynamic and flexible interaction is achieved in that the diaphragms are arranged movably relative to one other and can be moved with respect to one another as required for the individual application thus resulting in a different collimation effect.

At least one embodiment of the invention further relates to a filter apparatus for forming an intensity profile of the X-ray bundle. This filter apparatus may have a filter which, in turn, has one or more filter elements.

This filter apparatus can be combined with the above-described diaphragm apparatus. However, the filter apparatus represents an individual aspect of at least one embodiment of the invention, which is also disclosed herein independently of the diaphragm apparatus and can be used independently. To form an intensity profile of the X-ray bundle, the filter apparatus according to an embodiment of the invention comprises two filter elements mounted so as to be positionable with respect to one another and to be arrangeable in series in the X-ray direction, which are in each case shaped such that that, as soon as they are arranged completely superimposed in the X-ray direction, they form a complete filter profile.

In the case of superimposition in the direction of radiation of a diaphragm aperture of a diaphragm and the filter for forming the intensity profile of the filter apparatus inside the X-ray bundle, a desired overlaying (according to the diaphragm aperture) and forming of the beam profile can be achieved simultaneously without having to provide further mechanical components for the X-ray device.

A further embodiment of the invention provides that one of the diaphragms comprises at least one further aperture comprising a filter for forming the energy spectrum of the X-ray bundle. With superimposition in the direction of radiation of a diaphragm aperture of a diaphragm and the filter for forming the X-ray beam spectrum of the other diaphragm within the X-ray bundle, it is possible to achieve a desired superimposition (according to the diaphragm aperture) and an adaptation of the beam spectrum likewise simultaneously without having to provide further mechanical components for the X-ray device.

According to one preferred embodiment of the filter apparatus, the filter for forming the intensity profile of the X-ray bundle comprises at least two filter elements mounted so as to be positionable with respect to one another and filter elements arranged or arrangeable in series in the X-ray direction, which are in each case shaped such that that, as soon as they are arranged completely superimposed in the X-ray direction, they form a complete filter profile.

In other words, in this embodiment, the filter for forming the beam profile is arranged so as to be individually positionable. The individual filter elements can therefore be introduced individually into the X-ray beam as long as the filter aperture of the filter apparatus is already located within the beam path or the two filter elements can be superimposed in the direction of radiation. This enables an individual filtering effect to be set in dependence on the position of the filter elements with respect to one another.

A complete filtering effect is achieved only when the two filter elements are completely superimposed in the beam direction. In this context, a complete filtering effect means a maximum attenuation of the intensity of the X-rays which is, in particular, homogeneous over the beam cross section. When the diaphragm apparatus according to at least one embodiment of the invention and the filter apparatus according to at least one embodiment of the invention are combined, it is possible for the filter elements to be positionable in the positioning direction of the diaphragms or, depending upon the application, also transverse to the positioning direction of the diaphragms.

It is in particular preferable for the filter apparatus according to at least one embodiment of the invention for forming the intensity profile of the X-ray bundle to generate an intensity profile, which varies or is variably adjustable with reference to a direction transverse to the feed direction, i.e. in the $\varphi$ direction.

This variant can be adapted particularly flexibly to the circumstances of an examination object. For example, the special absorption behavior of an examination object or the extension of the region of the examination object to be depicted can be taken into account. However, this requires a further moving mechanism. The filtering effect is in particular steplessly selectable or adjustable.

In this context, the shape of the filter elements is in principle arbitrary, however it is preferably side-inverted or complementary with reference to the positioning direction of the filter elements. The filter elements can in particular be embodied as ramp-shaped with an ascent that is constant or variable over the width of the filter element. Other filter element shapes, for example a step-shaped course or mixed shapes made up of sub-regions with different shapes are however also possible and within the meaning of embodiments of the invention.

According to another preferred embodiment of the invention, instead of filter elements for forming the X-ray profile on a diaphragm, the diaphragm apparatus comprises at least one further diaphragm arranged in the X-ray direction in front of, behind or between the other diaphragms, said further diaphragm being mounted so as to be positionable with respect to the other diaphragms and having an aperture comprising a second filter for forming the intensity profile of the X-ray bundle. In this context, the first and the second filters for forming the intensity profile of the X-ray bundle are such that, as soon as they are arranged completely superimposed in the X-ray direction, they form a complete filter profile. This variant has the advantage compared to the above-described embodiment that the additional diaphragm comprising the second intensity profile filter can comprise further apertures for an alternative overlaying and/or filter, which can be used with other examinations with the X-ray device when the second filter is not required for forming the intensity profile. This enables space and mechanical components to be saved.

At least one embodiment of the invention further relates to an X-ray device for scanning an examination object via an X-ray bundle comprising a diaphragm apparatus according to at least one embodiment of the invention.

In one particularly preferred variant of at least one embodiment, the X-ray device is embodied as a computed tomography device or a C-arm X-ray device.

In one particularly preferred variant of at least one embodiment, the medical imaging system is embodied as an X-ray computed tomography scanner or as a C-arm X-ray device.

FIG. 1 shows an X-ray device, here a computed tomography scanner, partially in a block view and partially in a perspective view. Its recording system comprises a radiator 15, for example in the form of an X-ray tube with a diaphragm apparatus 1 close to the source and a detector 13 embodied as a panel-like array. Here, the array comprises a plurality of detector elements 14 assigned to rows and columns, wherein only one of these is given a reference character.

The radiator 15 and the detector 13 are attached opposite to one another in a rotating frame, which is not explicitly depicted, and is called a gantry such that, during the operation of the computed tomography scanner, a fan-shaped beam bundle 10 emitted by a focus 12 of the radiator 15 and overlaid through the diaphragm apparatus 1, arrives at the detector 13. In each case, the detector elements 14 generate an attenuation value dependent upon the attenuation of the radiation passing through the scan region, which is referred to in the following as a scanning value. The conversion of the radiation into scanning values is performed, for example via a photodiode that is optically coupled to a scintillator or via a directly converting semiconductor. A set of scanning values of the detector 13 is called a projection.

The rotating frame can be rotated via a drive device (not shown) controlled by a control unit 18 about a system axis 11 in the $\varphi$ direction shown. This enables a plurality of projections to be prepared from different projection directions of an examination object 2 arranged in the scanning region of the recording system. The rotation of the gantry with a simultaneous continuous feeding of the examination object 2 in the direction of the system axis 11 in particular enables the scanning of an examination volume of the examination object 2, which is larger than the scanning region formed by the recording system. The scanning values for the projections are read out by a data acquisition unit 16 and forwarded to a computing unit 17 for the calculation of a reconstructed image. The reconstructed image can be visualized to an operator on a display unit 19.

Without, for example, a dynamic masking out of a part of the beam bundle 10 emitted by the radiator 15, during a run-in and an after-run, regions of the examination object 2 are irradiated which do not make any contribution to the reconstruction of the image and so the examination object 2, for example a patient, is exposed to unnecessary radiation from X-rays during these segments of the spiral scanning 5.

For flexible adjustability of the overlaying of the X-ray bundle 10 during a scanning process, the diaphragm apparatus 1 according to an embodiment of the invention comprises two different diaphragms 3, 4.

In this example embodiment, the two diaphragms 3, 4 are mounted transverse to the feed direction 20 (z-axis of the coordinate system depicted) or transverse to the system axis 11 (along the x-axis of the coordinate systems depicted) so as to be positionable with respect to one another. Mounting or positionability of this kind results in an adjustment of the X-ray fan width along the x-axis. Alternatively, but not shown in any more detail here, the two diaphragms are aligned along the z-axis of the coordinate system, i.e. along the feed direction 20, and mounted along this so as to be positionable with respect to one another, i.e. in particular independently of one another. This mounting results in adjustability of the height of the X-ray fan 10. In each case of the example embodiment, the positioning direction of the diaphragms 3, 4 is perpendicular to the direction of the X-rays oriented on the central beam of the X-ray fan.

The second diaphragm 4 is arranged closer to the focus 12 than the first diaphragm 3 so that even small positioning movements of the second diaphragm 4 can achieve large changes in the fan geometry. In principle, obviously diaphragm apparatuses according to an embodiment of the invention can also be implemented with an inverse arrangement of the diaphragms 3, 4.

The diaphragms 3, 4 can be embodied positionably such that a very precise adjustment of the overlaying of the beam bundle 10 can take place. For example, each diaphragm 3, 4 can in each case interact with a positioning motor (not shown) provided for this purpose and which has an adjusting precision of a few micrometers. However, as a rule, the high adjusting precision is achieved at the expense of rapid dynamic positioning of the diaphragm elements. Alternatively and depending upon the application, however, rapid positioning speeds of, for example, several centimeters a second are required. Rapid dynamic masking-out of a corresponding part of the beam bundle 10 can, therefore, be achieved, for example, by the use of corresponding positioning motors. The high positioning speed can, however, also result in higher tolerances for the adjustable precision of the position of diaphragms 3, 4. Therefore, the person skilled in the art should select suitable motors taking account of the possible tolerances.

The displacement of the diaphragms via the positioning motors is possible in a simple way, for example, if the two diaphragms 3, 4 are in each case mounted on a track system.

During the operation of the computed tomography scanner, the thermal stress on the radiator 15 can result in the focus 12 being displaced from its original position. For this reason, the two diaphragms 3, 4 are mounted so as to be positionable parallel to one another. This enables a displacement of the focus 12 of the X-rays to be taken into account in a simple way.

The two diaphragms 3, 4 in each case comprise at least one diaphragm aperture and a region impermeable to X-rays, as will be demonstrated in more detail in the following figures.

The example embodiment of the diaphragm apparatus 1 according to an embodiment of the invention shown in FIG. 2 comprises a first and a second diaphragm 3, 4. Similarly to the depiction in FIG. 1, these are mounted along the z-axis and transverse to the x-axis, i.e. parallel to the system axis 11 independently of one another and hence also so as to be positionable with respect to one another. Each of the diaphragms 3, 4 comprises at least one diaphragm aperture 3.1, 4.1 corresponding to maximum collimation. These, in each case in the positioning direction, have the largest diaphragm aperture on the diaphragms 3, 4 and hence have maximum permeability to the X-ray fans 10. The diaphragm apertures 3.1 and 4.1 are in particular of the same size in the positioning direction, but can, however, also have different extensions, for example corresponding to a distance of the diaphragms 3, 4 in the X-ray direction. Each of the diaphragms 3, 4 also further comprises a region 3.0, 4.0 that is impermeable to X-rays. This region in each case comprises the same aperture size in the positioning direction as the diaphragm aperture 3.1, 4.1. The regions 3.0 and 4.0 are also arranged immediately adjacent to the diaphragm apertures 3.1, 4.1 and in the positioning direction are located on opposite sides of the diaphragm apertures 3.1, 4.1.

The positioning of the two diaphragms 3, 4 or of only one of the diaphragms enables the diaphragm apertures 3.1, 4.1 to be superimposed in the beam direction corresponding to maximum collimation. Alternatively, the diaphragm apertures 3.1, 4.1 can be at least partially superimposed with the regions 3.0, 4.0 impermeable to X-rays thus resulting in collimations smaller than the maximum collimation. Targeted positioning of the two diaphragms 3, 4 in the X-ray bundle 10 enables specific parts of the X-ray beam to be overlaid or masked out. This means an embodiment of the invention can be used particularly flexibly.

Optionally, the diaphragm 3 comprises a further diaphragm aperture 3.2 with an extension in the positioning direction smaller than the extension of the diaphragm aperture 3.1. This causes a masking-out in the X-ray beam of a correspondingly larger part of the X-ray bundle 10. The diaphragm 3 also optionally comprises an aperture in which a filter 3.3 is arranged. This can be provided for spectral filtering of the X-ray bundle 10 and/or for forming the intensity profile of the X-ray bundle 10. The diaphragm 4 also optionally comprises a further diaphragm aperture 4.2 with a smaller extension than the diaphragm aperture 4.1 and/or a further aperture with a filter 4.3. Obviously, it is also possible for further diaphragm apertures (not shown) to be provided for each diaphragm 3, 4 and/or further apertures (not shown) for filters for each diaphragm 3, 4.

Depending upon the adjustment of the positions of diaphragms 3, 4, in this way it is possible particularly flexibly to achieve different collimations and/or filterings of the X-ray bundle 10 with only two independently-operating positioning drives. This permits a broad spectrum of use of the diaphragm apparatus 1 in a wide variety of applications. In particular, it is possible for a dynamic collimation, i.e. a change in the collimation during an examination, to be effected for example in dependence on the direction of projection cp. In particular, it is also possible for different collimations determined by a diaphragm aperture of one of the diaphragms 3, 4 to be combined with different filters. Alternatively, collimation can be achieved via two diaphragm apertures in the two diaphragms 3, 4.

The interaction of the two diaphragms 3, 4 can also achieve a positive saving of installation space and an increase in the adjusting speed since positioning paths can be advantageously shortened.

The example embodiment of a filter apparatus 21 according to an embodiment of the invention shown in FIG. 3 differs from the diaphragm apparatus shown in FIG. 2. In FIG. 3, the diaphragm apparatus is arranged in the beam fan 10 of the radiator 15 emitted by the focal point 12. The diaphragm apparatus 21 comprises two filter elements 23, 24 which are independently positionable with respect to one another in the positioning direction. In this example embodiment, the positioning direction extends transverse to the feed direction (or transverse to the z direction). Expressed another way, the positioning direction extends in the $\varphi$ direction.

The filter elements 23, 24 have a ramp shape with a variable ascent in the positioning direction, wherein the ramps are arranged inverted in the positioning direction. Together they form the filter 3.4, which represents a filter for forming the intensity profile of the X-ray bundle 10. This enables an intensity profile to be effected transverse to the feed direction (or transverse to the z direction) via the fan beam in the $\varphi$ direction.

A corresponding adjustment of the filter elements 23, 24 now enables an individual beam profile to be generated in that the two filter elements 23, 24 in the beam path are superimposed to a greater or lesser extent. The individual adjustability of the two filter elements 23, 24 enables the particular shape or the individual absorption behavior of an examination object 2 to be taken into account particularly effectively. To this end, shapes of the filter elements other than the shape shown here are possible. For example, ramp shapes with a constant ascent, stepped shapes or other types of free-form courses can be used as long as they appear suitable for the adjustment of a desired intensity profile.

In particular, the two filter elements A, B do not, as depicted, have to have mirror-symmetrical or rotationally-symmetrical shapes, but can have any shaped desired compared one another. The filter elements A, B can be positioned individually, i.e. independently of one another or synchronously, i.e. coupled to one another (for example via a common positioning motor and a corresponding positioning actuator) into our out of the beam path. This embodiment effects a stepless adjustability of wedge contours.

In addition, the much disputed 'size specific dose estimate' (SSDE), can, for example be set specifically as an optimization variable or kept constant. Therefore, the embodiment permits an adjustment of the wedge profile in dependence on the direction of projection cp.

This embodiment permits the operation of different beam geometries with only one diaphragm box or filter design, for example with different distance from the filter and beam focus. This has cost advantages. Movement paths for the filter elements 23, 24 are correspondingly short. However, this embodiment of the diaphragm apparatus requires additional positioning motors and corresponding positioning mechanics or actuators to effect the displacement of the filter elements 23, 24, but which, in principle, do not differ from the positioning motors actually to be used for the diaphragms 3, 4. A subsequent retrofitting or upgrading of the form filter is easy to implement in this variant.

The embodiment of the filter apparatus described with reference to FIG. 3 can be combined with the embodiment of the diaphragm apparatus described with reference to FIG. 2. In this context, the positioning direction of the filter elements 23, 24 of the diaphragm apparatus 21 can be provided perpendicular to the system axis z and the positioning direction of the diaphragms 3, 4 of the diaphragm apparatus 1 parallel to the system axis z. In a combined apparatus of this kind, it is possible, on the one hand to achieve the generation of an intensity profile of the radiation in the direction by the filter elements 23, 24 and, on the other hand, collimation in the z direction by the diaphragm apparatus 1.

The embodiment of the filter apparatus described with respect to FIG. 3 can, however, also be used separately from a—as, for example, described with reference to FIG. 2—diaphragm apparatus and is also described and disclosed separately therefrom.

Moreover, it would also be possible for a first filter element 23 to be assigned to a first diaphragm 3 and a second filter element 24 to a second diaphragm 4.

Where advisable and in the context of the invention, individual example embodiments, individual partial aspects thereof, can also be combined with one another without departing from the scope of the present invention. Where transferrable, advantages of the invention described with respect to one example embodiment also apply without being expressly cited to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A diaphragm apparatus for a collimation of an X-ray bundle of an X-ray device provided for scanning an examination object, the diaphragm apparatus comprising:
    two diaphragms, each in the form of slotted diaphragms, arranged in series in a feed direction of the X-rays and each of the two diaphragms being positionable with respect to one another, wherein each of the two diaphragms includes
        a fixed diaphragm aperture corresponding to maximum collimation of the X-ray bundle, and
        a region impermeable to X-rays, including an extension corresponding to diaphragm aperture corresponding to the maximum collimation, wherein the two diaphragms are mounted movably in a direction transverse to a feed direction of the X-ray device.

2. The diaphragm apparatus of claim 1, wherein the region impermeable to X-rays, of one diaphragm of the two diaphragms, is arranged in respect of a positioning direction on one side of the diaphragm aperture corresponding to the maximum collimation and wherein the region impermeable to X-rays, of the other diaphragm of the two diaphragms, is arranged in respect of a positioning direction on another side of the diaphragm aperture corresponding to the maximum collimation.

3. The diaphragm apparatus of claim 2, wherein at least one of the two diaphragms comprises a further fixed diaphragm aperture corresponding to a collimation relatively smaller than the maximum collimation.

4. The diaphragm apparatus of claim 2, wherein the two diaphragms are mounted parallel so as to be positionable with respect to one another.

5. The diaphragm apparatus of claim 2, wherein the collimation of the X-ray bundle is adjustable via only one diaphragm.

6. The diaphragm apparatus of claim 2, wherein the collimation of the X-ray bundle can be adjusted via both diaphragms.

7. The diaphragm apparatus of claim 2, wherein one of the two diaphragms includes at least one further aperture comprising a filter for forming the intensity profile of the X-ray bundle.

8. The diaphragm apparatus of claim 2, wherein one of the two diaphragms includes at least one further aperture comprising a filter for forming the energy spectrum of the X-ray bundle.

9. The diaphragm apparatus of claim 2, further comprising a filter apparatus with two filter elements mounted to be positionable with respect to one another and arrangeable in series in the X-ray direction, each of the two filter elements being shaped such that, as soon as they are arranged completely superimposed in the X-ray direction, the two filters form a complete filter profile.

10. An X-ray device for scanning an examination object by way of an X-ray bundle, comprising
    the diaphragm apparatus of claim 9.

11. The X-ray device of claim 10, wherein the X-ray device is embodied as a computed tomography device or C-arm X-ray device.

12. An X-ray device for scanning an examination object by way of an X-ray bundle, comprising
    the diaphragm apparatus of claim 2.

13. The X-ray device of claim 12, wherein the X-ray device is embodied as a computed tomography device or C-arm X-ray device.

14. The diaphragm apparatus of claim 1, wherein at least one of the two diaphragms comprises a further fixed diaphragm aperture corresponding to a collimation relatively smaller than the maximum collimation.

15. The diaphragm apparatus of claim 1, wherein the two diaphragms are mounted parallel so as to be positionable with respect to one another.

16. The diaphragm apparatus of claim 1, wherein the collimation of the X-ray bundle is adjustable via only one diaphragm.

17. The diaphragm apparatus of claim 1, wherein the collimation of the X-ray bundle can be adjusted via both diaphragms.

18. The diaphragm apparatus of claim 1, wherein one of the two diaphragms includes at least one further aperture comprising a filter for forming the intensity profile of the X-ray bundle.

19. The diaphragm apparatus of claim 1, wherein one of the two diaphragms includes at least one further aperture comprising a filter for forming the energy spectrum of the X-ray bundle.

20. The diaphragm apparatus of claim 1, further comprising a filter apparatus with two filter elements mounted to be positionable with respect to one another and arrangeable in series in the X-ray direction, each of the two filter elements being shaped such that, as soon as they are arranged completely superimposed in the X-ray direction, the two filters form a complete filter profile.

21. An X-ray device for scanning an examination object by way of an X-ray bundle, comprising
    the diaphragm apparatus of claim 20.

22. The X-ray device of claim 21, wherein the X-ray device is embodied as a computed tomography device or C-arm X-ray device.

23. An X-ray device for scanning an examination object by way of an X-ray bundle, comprising
    the diaphragm apparatus of claim 1.

24. The X-ray device of claim 23, wherein the X-ray device is embodied as a computed tomography device or C-arm X-ray device.

25. The diaphragm apparatus of claim 1, wherein each of the two diaphragms are independently movable in the direction transverse to the feed direction of the x-ray device via a motor.

26. The diaphragm apparatus of claim 1, wherein the direction transverse to the feed direction of the x-ray device is in a φ direction that is perpendicular to a system axis, and positioning direction of each of the two diaphragms is parallel to the system axis.

* * * * *